(12) United States Patent
 Guo et al.

(10) Patent No.: US 10,950,015 B2
(45) Date of Patent: Mar. 16, 2021

(54) MEDICAL IMAGE PROCESSING METHOD, AND COMPUTER READABLE STORAGE MEDIUM

(71) Applicant: General Electric Company, Schenectady (CN)

(72) Inventors: Bo Guo, Beijing (CN); Gang Fang, Beijing (CN); Xueli Wang, Beijing (CN)

(73) Assignee: General Electric Company, Schenectady, NY (US)

( * ) Notice: Subject to any disclaimer, the term of this patent is extended or adjusted under 35 U.S.C. 154(b) by 80 days.

(21) Appl. No.: 16/354,644

(22) Filed: Mar. 15, 2019

(65) Prior Publication Data

US 2019/0287278 A1  Sep. 19, 2019

(30) Foreign Application Priority Data

Mar. 16, 2018 (CN) .................. 2018102217520.6

(51) Int. Cl.
| | |
|---|---|
| *G06T 11/00* | (2006.01) |
| *G06T 7/00* | (2017.01) |
| *G06T 7/70* | (2017.01) |
| *A61B 6/03* | (2006.01) |
| *A61B 6/00* | (2006.01) |

(52) U.S. Cl.
CPC ............ *G06T 11/008* (2013.01); *A61B 6/032* (2013.01); *A61B 6/505* (2013.01); *A61B 6/5217* (2013.01); *A61B 6/5229* (2013.01); *G06T 7/0012* (2013.01); *G06T 7/70* (2017.01); *G06T 2207/10072* (2013.01); *G06T 2207/30012* (2013.01)

(58) Field of Classification Search
None
See application file for complete search history.

(56) References Cited

U.S. PATENT DOCUMENTS

2013/0322727 A1* 12/2013 Goto ..................... A61B 5/004
                                                        382/132

* cited by examiner

*Primary Examiner* — Leon Flores

(57) ABSTRACT

The present invention provides a medical image processing method and a computer-readable storage medium. The method includes: reconstructing a two-dimensional cross-sectional image of an imaged tissue based on a volumetric image of the imaged tissue; projecting a CT value of the imaged tissue along a normal direction of the centerline of the imaged tissue in the two-dimensional cross-sectional image; and, positioning the imaged tissue based on the projection result of the CT value of the imaged tissue.

8 Claims, 7 Drawing Sheets

MEDICAL IMAGE PROCESSING METHOD, AND COMPUTER READABLE STORAGE MEDIUM

CROSS-REFERENCE TO RELATED APPLICATIONS

This application claims priority to China patent application number 201810217520.6, filed on Mar. 16, 2018, the entirety of which is incorporated herein by reference.

FIELD

The invention relates to the field of medical imaging and detection, and in particular, to a medical image processing method and a computer-readable storage medium.

BACKGROUND

During medical image processing, it is often necessary to detect certain features of a target object (or an imaged tissue) in a medical image obtained from an imaging device such as a computed tomography (CT) device or a magnetic resonance (MR) device. For example, when a doctor diagnoses cervical lesions, it is necessary to determine the position information such as the center position, the inclination angle, and the thickness of the intervertebral disc based on the obtained medical images of the human cervical spine. In the prior art, sometimes one needs to manually operate on the image on an operation interface to obtain the position information described above. As shown in FIG. 11, after completion of the scout (positioning) image scanning, the doctor manually calibrates the position and inclination angle of each intervertebral disc on the scout image of the cervical spine, and then performs an axial scan or helical scan to extract slice images near each intervertebral disc to conduct an analysis for lesions. Examinations performed in this way may lead to different errors in manual calibration of the intervertebral disc parameters due to different experience and habits of the physicians. Meanwhile, the manual calibration method also causes a large number of repeated operations of the physician, which takes time and labor. Although some automatic detection technologies for imaged tissues have been developed in the prior art, the accuracy of the recognition and positioning needs to be further improved.

BRIEF DESCRIPTION

In view of the deficiencies of the prior art, the present invention aims to provide a medical image processing method so as to improve the accuracy and robustness of imaged tissue recognition and positioning.

One aspect of the present invention discloses a medical image processing method, comprising reconstructing a two-dimensional cross-sectional image of an imaged tissue based on a volumetric image of the imaged tissue; projecting a CT value of the imaged tissue along a normal direction of a centerline of the imaged tissue in the two-dimensional cross-sectional image; and positioning the imaged tissue based on the projection result of the CT value of the imaged tissue.

Another aspect of the present invention discloses a computer-readable storage medium configured to store a computer program, which is configured to execute the medical image processing method described above.

BRIEF DESCRIPTION OF THE DRAWINGS

The technical solutions of the present invention will be further described in detail below with reference to the accompanying drawings and embodiments.

DETAILED DESCRIPTION

In the following, specific embodiments of the present invention will be described. It should be noted that, in the detailed description of these embodiments, all features of the actual embodiments may not be described in detail for conciseness of the description. These embodiments are not intended to limit the scope of the claims of the present invention, but rather these embodiments are intended only to outline the possible forms of the present invention. Indeed, the subject matter of the present invention may encompass various forms that are similar or different from the following embodiments.

The present invention provides a medical image processing method that may be performed in a computer unit such as a CT imaging system to accurately position an imaged tissue, such as a vertebral body of a human body, based on an image obtained by scanning.

Figure 1:
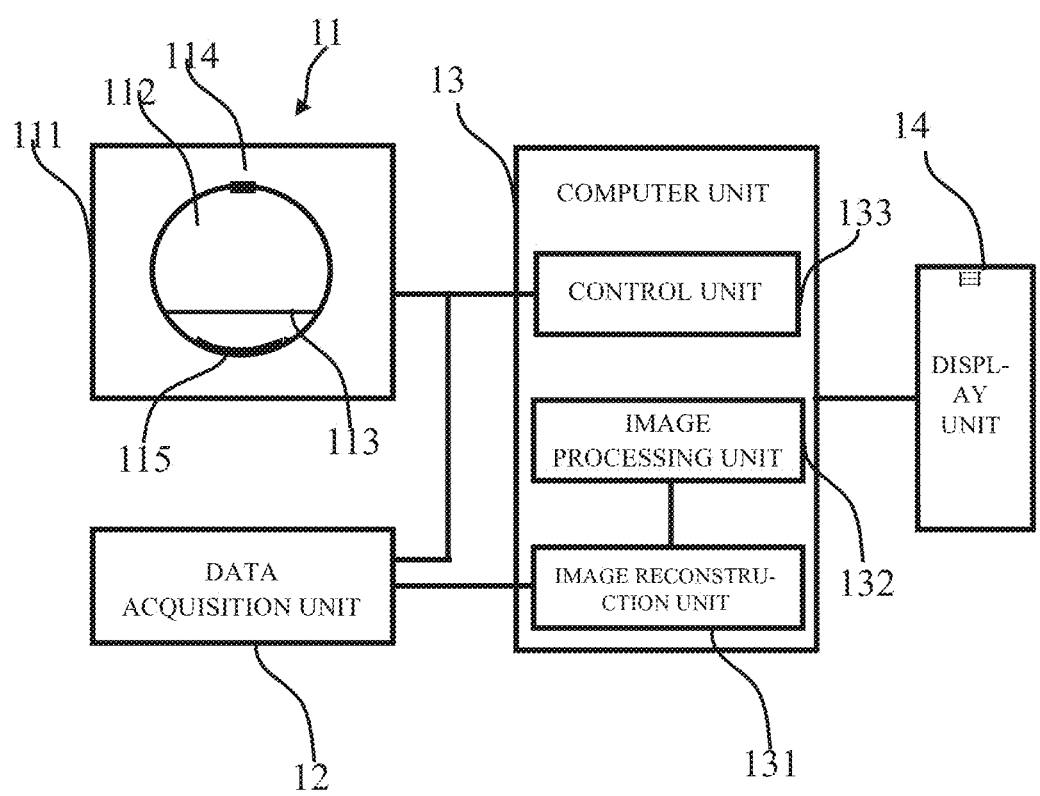
FIG. 1 shows a schematic diagram of a CT medical imaging system provided in an embodiment of the present invention.

FIG. 1 is a schematic diagram of a CT imaging system in an embodiment of the present invention. The CT imaging system as shown in FIG. 1 may include a scanning unit 11, which includes a gantry 111 formed with a cylindrical scanning chamber 112 to accommodate a patient and a patient table 113 to support the patient. A bulb 114 and a detector 115 are provided oppositely on the gantry 111. During the rotation of the gantry 111, X-rays emitted by the bulb 114 are received by the detector 115 after penetrating the human tissues, and the X-rays received by the detector 115 are converted into digital image signals.

The CT imaging system further comprises a data acquisition unit 12 for acquiring the digital image signal and transmitting the signal as CT raw image data to the image reconstruction unit 131 of the computer unit 13 for image reconstruction.

The image processing unit 132 in the computer unit may further process the reconstructed image to meet the requirements of medical diagnosis. Moreover, the reconstructed or processed image may be output to the display unit 14 for display.

The computer unit 13 may also includes a control unit 133 for controlling operating parameters, states, and the like of the scanning unit 11 and the data acquisition unit 12.

Figure 2:
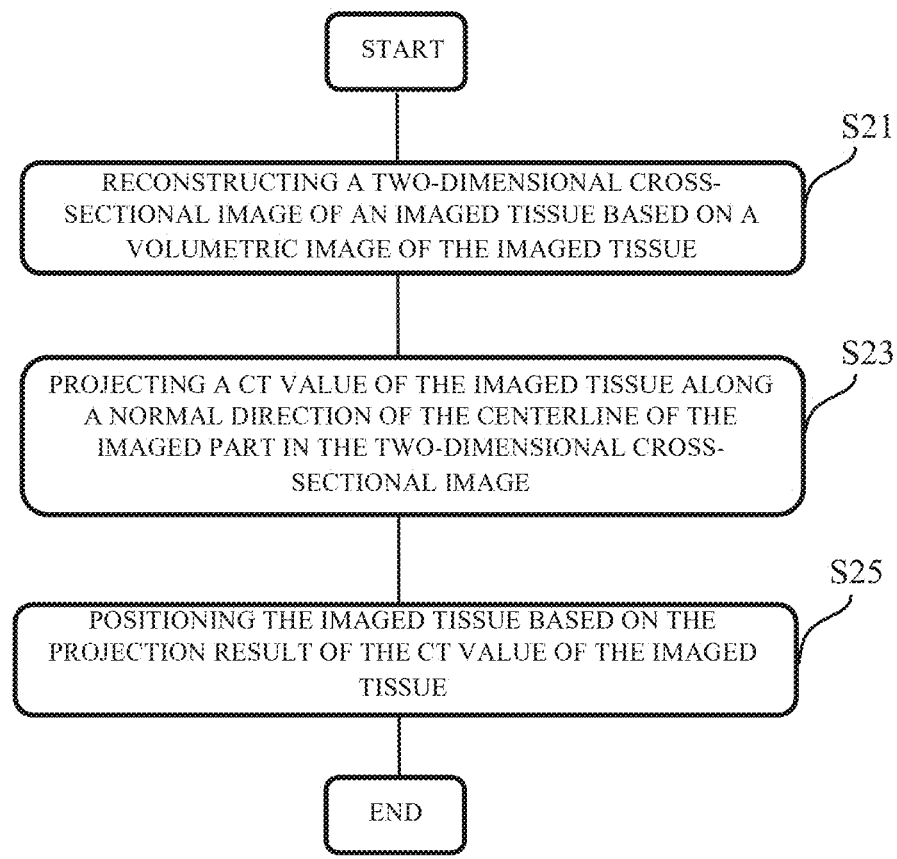
FIG. 2 shows a flowchart of a medical image processing method provided by an embodiment of the present invention.

FIG. 2 is a flowchart of an embodiment of a medical image processing method provided by the present invention. As shown in FIG. 2, the method includes the following steps S21, S23, and S25.

In step S21, a two-dimensional cross-sectional image of the imaged tissue is reconstructed based on the volumetric image of the imaged tissue. The volumetric image of the above-mentioned imaged tissue may include a plurality of successively acquired slices, which may be obtained based on a CT spiral scanning, a CT axis scanning or other scanning methods. Before the CT spiral scanning or a CT axis scanning, a low-dose Scout scan may be performed to obtain plain slices of human body, and the region of interest of the scan may be determined by the position of the imaged tissue in the plain slices, and then the volumetric image of the imaged tissue may be obtained through the three-dimensional scanning method described above.

In this embodiment, a two-dimensional cross-sectional view of the imaged tissue may be generated based on the position of the imaged tissue in different slices. Taking a human vertebral body as an example, the two-dimensional cross-sectional image may be a sagittal image of a human vertebral body.

In step S23, a CT value of the imaged tissue is projected along the normal direction of the centerline of the imaged part in the two-dimensional cross-sectional image.

Specifically, in step S21, a centerline of the imaged tissue may be formed based on a center position of the imaged tissue in the volumetric image, and a two-dimensional cross-sectional image may be generated along the centerline, such that there is centerline information in the generated two-dimensional cross-sectional image.

In step S25, the imaged tissue is positioned based on the result of the projection of the CT value of the imaged tissue.

The present invention takes the positioning of the vertebral body as an embodiment, and embodiments of the present invention will be specifically described with reference to the accompanying drawings. Those skilled in the art may also apply the positioning method disclosed in the present invention to image processing other spine (e.g., thoracic vertebrae, lumbar vertebrae), bones and interstitial bones, or other imaged tissues.

The vertebral body includes vertebrae and intervertebral discs. Specifically, in step S25, positioning the imaged tissue according to the result of the projection of the CT value of the imaged tissue includes: obtaining the position where the peak in the result of the projection is located, and positioning the center position between the positions of two adjacent peaks as an intervertebral disc position. Because the CT values of the vertebral and intervertebral disc tissues are significantly different and when they appear in the image, the vertebral tissue portion is brighter and the intervertebral disc tissue is darker. Therefore, in the result of the projection, the peak of the projection value is considered as the vertebral position, and the position between the two adjacent peaks is considered as the intervertebral disc. Through this projection in connection with the normal direction of the vertebral centerline, the intervertebral disc can be located quickly and accurately.

In order to further refine the above results of disc positioning, it is also possible to use the conventional features of the intervertebral discs and vertebrae (e.g., evenly spaced apart) to adjust the intervertebral disc positions. Specifically, in step S25, positioning the imaged tissue according to the result of the projection of the CT value of the imaged tissue further includes: comparing the distance between the adjacent disc positions with a predetermined maximum threshold and a predetermined minimum threshold, and when the distance between the intervertebral disc positions is less than the minimum threshold, one of the two adjacent disc positions is excluded; and when the distance between the intervertebral disc positions is more than the maximum threshold, a new intervertebral disc position is added to the two adjacent disc positions. In this way, erroneous or missed detection of the intervertebral disc due to metal or lesions may be eliminated, making the result of the detection more robust.

The maximum threshold and minimum threshold above may be dynamic thresholds, which may be dynamically determined according to the median of the distances between multiple adjacent intervertebral disc positions of the current patient. For example, an appropriate value may be added to the median to generate the maximum threshold, and an appropriate value may be subtracted from the median to generate the minimum threshold.

The dynamic thresholds may also be obtained based on a cloud. For example, the dynamic thresholds may be determined based on the median of the recorded distances of the intervertebral disc positions of multiple patients on the cloud. Of course, the multiple patients may be those who are automatically matched with the current patient according to patient information, or those who are automatically matched with the intervertebral disc of the current patient according to the patients' shape, distances, etc., of intervertebral discs. The cloud above may perform data transmission with the image processing unit 132 of the computer unit 13 through a cloud network.

Optionally, before step S23, the method may further comprise: binarizing the CT value of the imaged tissue in the two-dimensional cross-sectional image. For example, 1 may be assigned to a CT value greater than a specific value, and 0 may be assigned to a CT value smaller than or equal to a specific value. In this way, more accurate positioning results may be obtained with higher projection efficiency.

Optionally, in step S25, positioning the imaged tissue according to the result of the projection of the CT value of the imaged tissue further comprises: determining a center position of the intervertebral disc, an inclination angle of the intervertebral disc, and the thickness of the intervertebral disc according to the intervertebral disc position and the image characteristics of the vertebrae adjacent thereto. Specifically, for example, grayscale gradient information of the image and the continuity characteristics of the edge of the vertebral body may be used to obtain the positions of the upper and lower edges and corner points of the two vertebrae adjacent to each intervertebral disc, thereby accurately determining the three-dimensional parameter information of each intervertebral disc, including the above center position of the intervertebral disc, the inclination angle of the intervertebral disc (for example, the inclination angle of the intervertebral disc relative to a horizontal line) and the thickness of the intervertebral disc.

Figure 3:
FIG. 3 shows a positioning image of a cervical spine obtained according to an exemplary embodiment of the present invention.

The following is a further description of the present invention by taking CT imaging and processing of the patient's cervical spine to locate the cervical intervertebral disc as an example:

FIGS. 3-9 are images obtained at different stages of CT imaging and processing of the cervical spine in an embodiment of the present invention. A positioning scan (also called Scout scan, plain scan, etc.) of the patient's neck is initially performed by a scanning unit of the CT imaging system, and a positioning image shown in FIG. 3 is obtained. Based on the positioning image, a region of interest may be manually or automatically determined by a computer unit, which in this example includes the patient's cervical spine.

Figure 4:
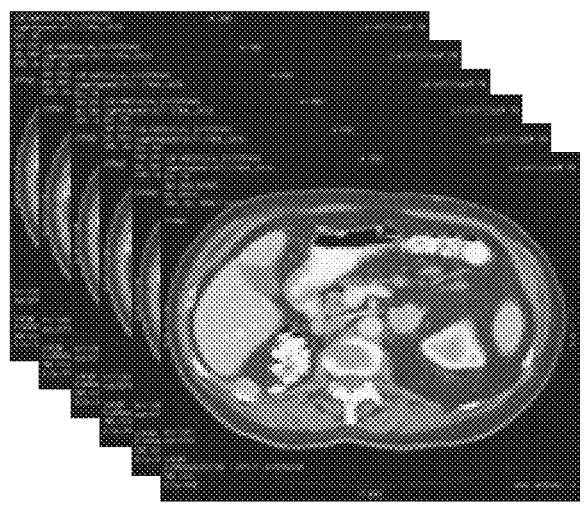
FIG. 4 shows a volumetric image of a cervical spine obtained according to an exemplary embodiment of the present invention.

The scanning unit 12 performs a helical scan on the patient based on the region of interest, and an image reconstruction unit 131 in the computer unit 13 performs image reconstruction based on the helical scan data, acquiring a volumetric image as shown in FIG. 4.

Figure 5:
FIG. 5 shows a sagittal two-dimensional cross-sectional image of a cervical spine obtained according to an exemplary embodiment of the present invention.

Based on the volumetric image, the image processing unit 132 in the computer unit 13 may identify the cervical spine in each slice of the volumetric image and determine the central position of the cervical spine, i. e., the position of the center of the cervical spine in the volumetric image. Based on the results of the identification and the determination of the center position, a sagittal two-dimensional cross-sectional image of the cervical vertebrae as shown in FIG. 5 may be reconstructed. It can be clearly seen from the sagittal two-dimensional cross-sectional images that the cervical vertebrae are vertically distributed on the vertebral body centerline.

Figure 6:
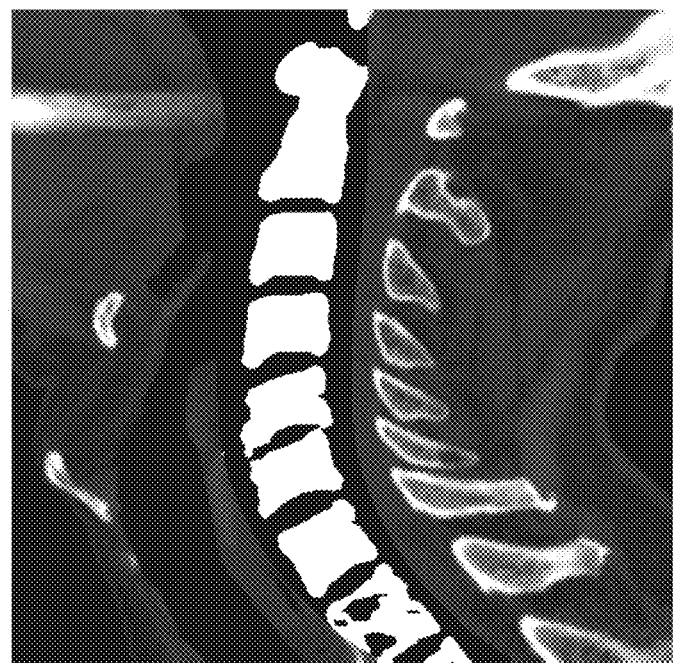
FIG. 6 shows a binarized image acquired according to an exemplary embodiment of the present invention.

The image processing unit 132 further performs binary segmentation of the cervical vertebra in the sagittal two-dimensional cross-sectional image to obtain a binarized image as shown in FIG. 6. Among them, a plurality of white irregular quadrilaterals located in the center of the image are cervical vertebrae, and black gaps between the white vertebrae are cervical intervertebral discs.

Figure 7:
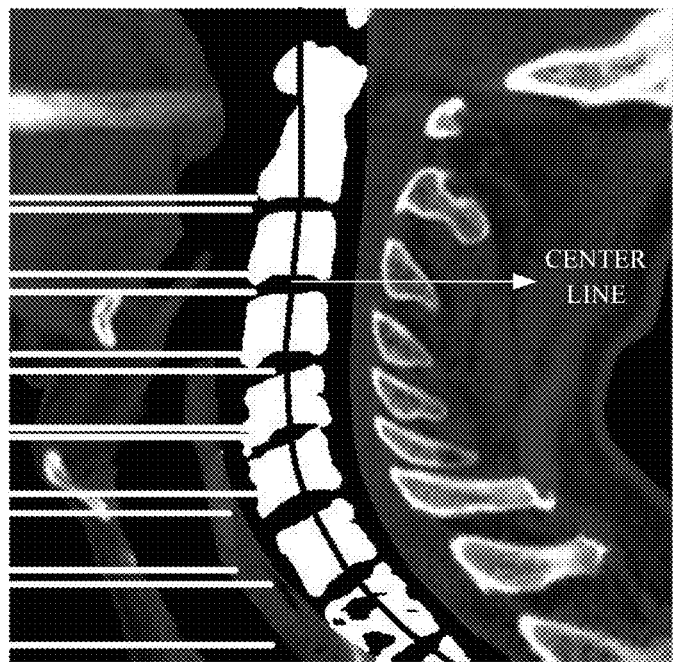
FIG. 7 shows a schematic view of a CT value projection along a normal direction of a centerline of a cervical vertebra body according to an exemplary embodiment of the present invention.
Figure 8:
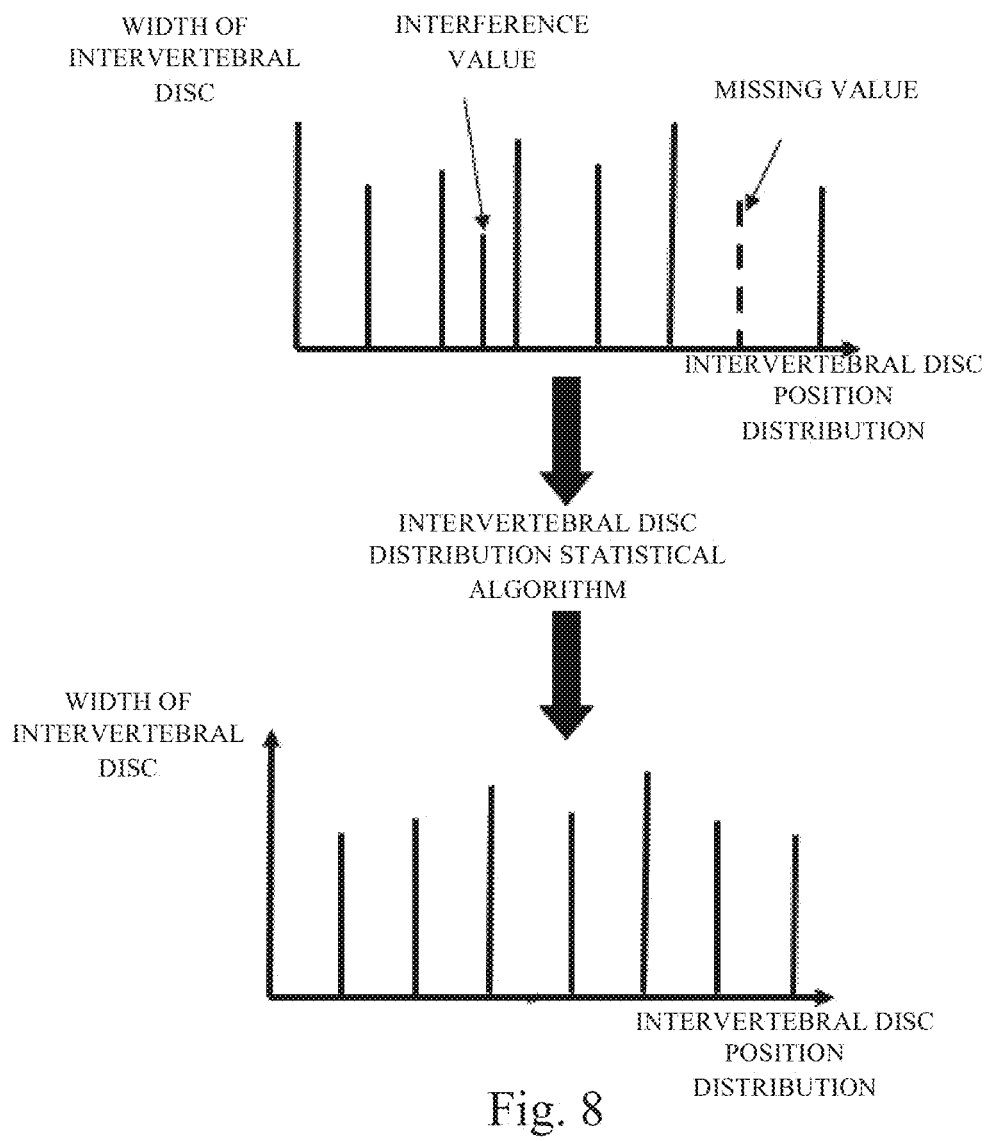
FIG. 8 shows a schematic diagram of a distribution sequence of an intervertebral disc obtained according to an exemplary embodiment of the present invention.

As shown in FIG. 7, the image processing unit selects the target region near the centerline of the vertebral body in the binarized image, wherein the target region can at least cover the vertebrae and the intervertebral disc, and the CT value of the binarized cervical vertebra body is projected along the normal direction of the centerline of the vertebral body (as shown by the arrows) (i. e., the cumulative CT value in the normal direction). A plurality of peak positions are acquired. During this process, only peak position at the intersection of zero value and a positive value in the result of the projection may be left, and the center between two nearest adjacent peak positions is initially positioned as the intervertebral disc position. Similarly, after the positioning of all the cervical intervertebral discs in the target area is completed, an original distribution sequence of intervertebral disc positions as shown in FIG. 8 may be estimated. The "nearest adjacent" mentioned above means that, as shown in FIG. 7, for the current peak, it has two adjacent peaks, wherein one of the adjacent peaks is farther and the other is closer, and in this embodiment, the closer adjacent peak will be considered as the nearest adjacent peak of the current peak.

As described above, in order to make the results of the positioning of the intervertebral discs more accurate, the results of the above positioning may be further modified after the positioning of all the intervertebral discs in the above target region is completed. As shown in the upper diagram of FIG. 8, the image processing unit 132 considers the peak value of the CT value in the normal direction of the central curve of the intervertebral disc as the width of intervertebral disc, and calculates and counts the distance between each intervertebral disc and its adjacent intervertebral discs according to the preliminarily estimated position of each intervertebral disc. The original distribution sequence will be processed according to a cervical disc distribution statistical algorithm to obtain a refined intervertebral disc distribution sequence shown in the lower diagram of FIG. 8. For example, the median of the distances between multiple adjacent intervertebral discs is used as a primary distance, and the dynamic thresholds, i.e., the maximum threshold and the minimum threshold, are set based on the primary distance. If the preliminary calculated distance between adjacent cervical intervertebral discs is less than the minimum threshold, then one of the adjacent cervical intervertebral disc positions (such as the interference value position as shown in the upper diagram of FIG. 8) will be removed. If the preliminary calculated distance between adjacent cervical intervertebral discs is more than the maximum threshold, then one intervertebral disc position (such as the missing value position as shown in the upper diagram of FIG. 8) will be inserted, thereby resulting in a distribution sequence as shown in the lower diagram of FIG. 8.

Figure 9:
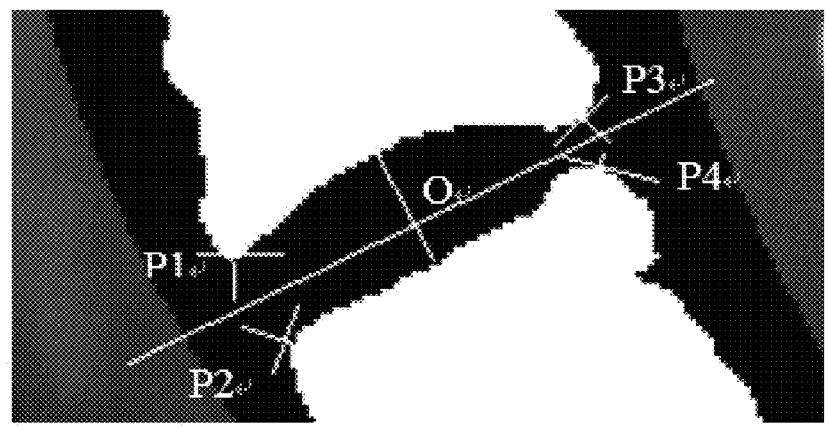
FIG. 9 shows a schematic diagram of determining the position center, angle and thickness of the intervertebral disc according to an exemplary embodiment of the present invention.

Further, as shown in FIG. 9, in the binarized image, for each of the intervertebral discs, using the image grayscale gradient information, the image processing unit 132 can find two corner points (P1, P2) to its left side, two corner points (P3, P4) to the right side, one center point of the connection line between the two left corner points (P1, P2) and another center point of the connection line between the two right corner points (P3, P4). A straight line may be generated based on the two center points, which is determined to be the centerline bisecting the two vertebrae. The center position (0) of the straight line relative to the two center points is the center position of the intervertebral disc. The inclination angle of the line is the inclination angle of the intervertebral disc. The value obtained by calculating the sum of the shortest distances between the central position (0) of the intervertebral disc and the two vertebral bodies is the thickness of the intervertebral disc.

Figure 10:
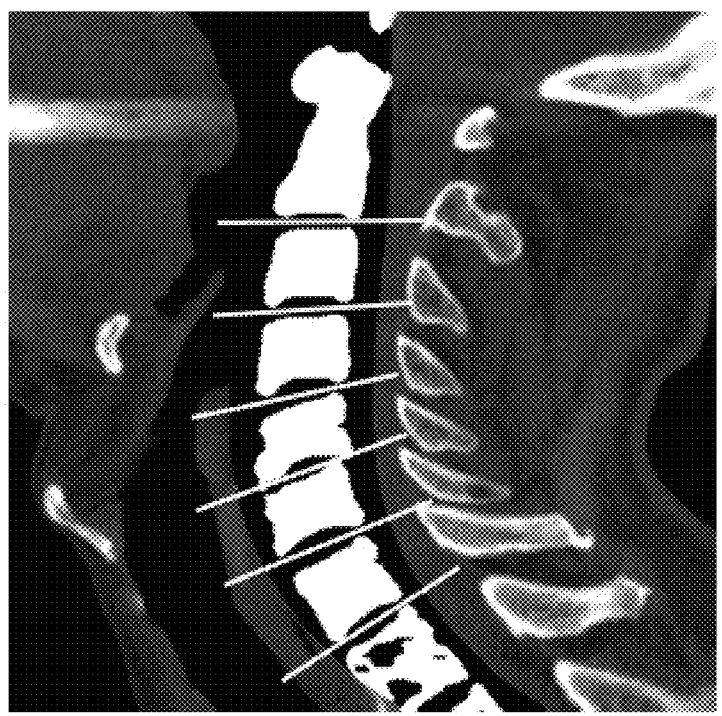
FIG. 10 shows a schematic diagram of an intervertebral disc position according to an exemplary embodiment of the present invention.

After the position of the intervertebral disc is determined, the position of the intervertebral disc is marked on the binarized image by an image processing unit. For example, the white line segment shown in FIG. 10 indicates the position of the cervical intervertebral disc and is displayed on the display unit 14.

Figure 11:
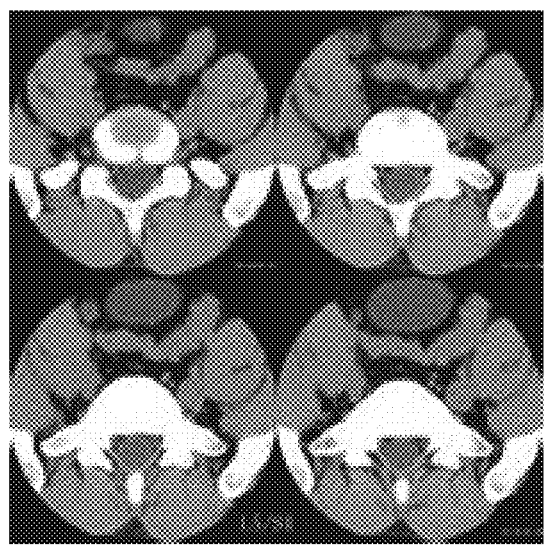
FIG. 11 shows a coronal slice image of an intervertebral disc obtained by image reconstruction along a calibration direction according to an exemplary embodiment of the present invention.
Figure 12:
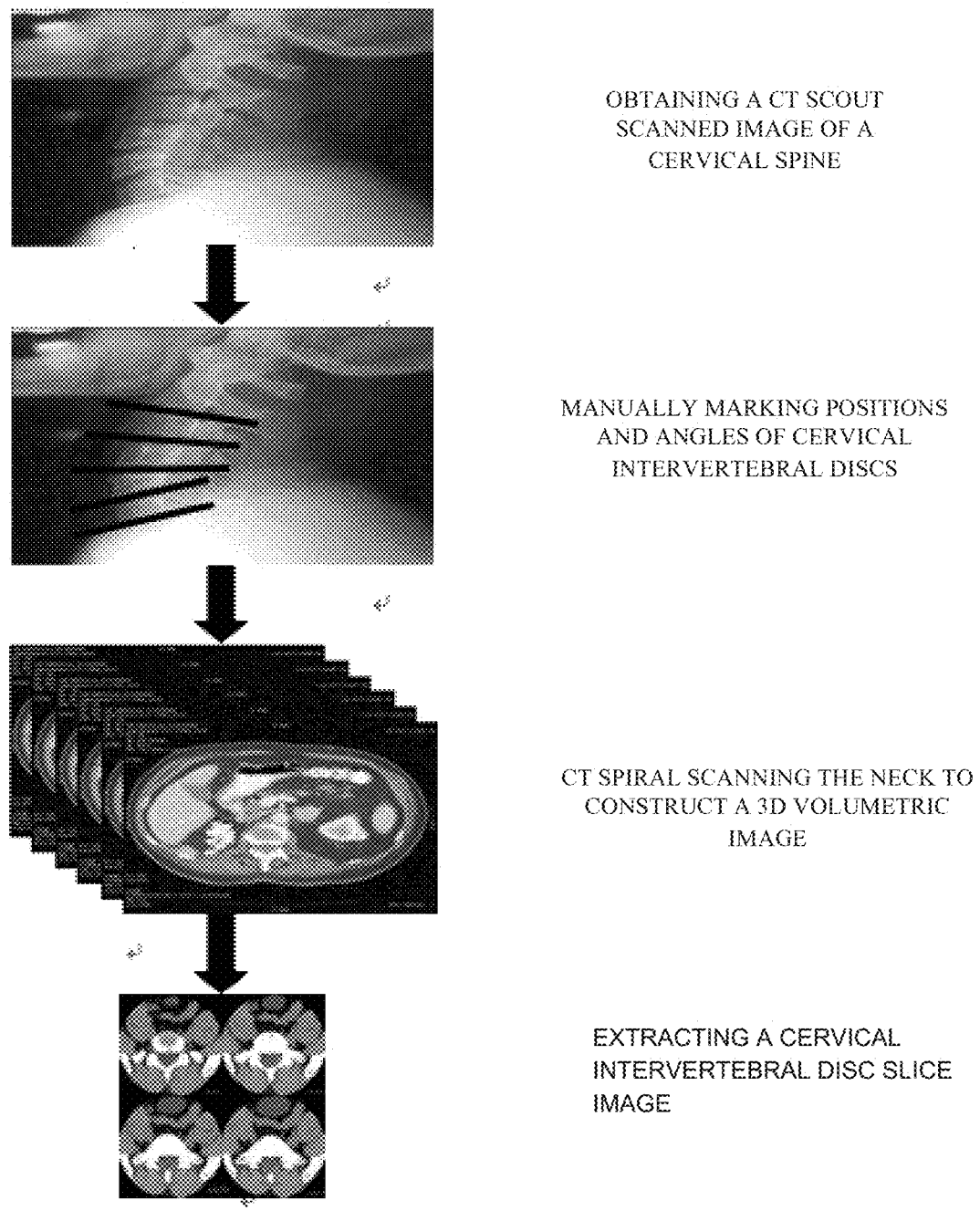
FIG. 12 shows a flowchart of CT imaging and positioning of a cervical spine in the prior art.

Based on the marked position of the intervertebral disc, a slice image may be reconstructed along the marked direction to obtain a coronal slice image of the intervertebral disc as shown in FIG. 11, for the doctor to perform lesion analysis.

It will be appreciated by those skilled in the art that, in the above stages, image processing performed based on the binarized image may instead be performed directly on the two-dimensional sectional image that has not been binarized.

An embodiment of the present invention also discloses a computer-readable storage medium, which may be installed in a computer unit of the above CT imaging system and used to store a computer program, wherein the computer program is at least configured to execute the above medical image processing method. The method includes the following steps: reconstructing a two-dimensional cross-sectional image of the imaged tissue based on a volumetric image of the imaged tissue; projecting a CT value of the imaged tissue along a normal direction of the centerline of the imaged tissue in the two-dimensional cross-sectional image; and positioning the imaged tissue based on the projection result of the CT value of the imaged tissue.

Further, prior to projecting the CT values of the imaged tissue, the computer program is further configured to perform binarization of CT values on the imaged tissue in the two-dimensional cross-sectional image.

Further, the computer program is further configured to determine the centerline of the imaged tissue in the two-dimensional cross-sectional image based on the position of the center of the imaged tissue in the volumetric image.

Further, the imaged tissue includes a vertebral body, which includes vertebras and intervertebral discs. The computer program is further configured to: obtain the position of the peak in the result of the projection, and position a center position between the positions of two adjacent peaks as the position of an intervertebral disc.

Further, the computer program is further configured to: compare the distance between adjacent intervertebral disc positions to a maximum threshold and a minimum threshold, and remove one of the two adjacent intervertebral disc positions when the distance between the two adjacent intervertebral disc positions is less than the minimum threshold; and add a new intervertebral disc position between two adjacent intervertebral disc positions when the distance between the two adjacent intervertebral disc positions is greater than the maximum threshold.

Further, the computer program is further configured to dynamically determine the maximum threshold and minimum threshold based on a median of a plurality of distances between adjacent intervertebral disc positions.

Further, the maximum threshold is determined according to the median of the plurality of distances between adjacent intervertebral disc positions of the vertebral body of the current patient, or is based on the median of the plurality of distances between adjacent intervertebral disc positions of vertebral bodies of multiple patients retrieved from the cloud.

Further, the computer program is further configured to: determine the position center, inclination angle, and thickness of the intervertebral disc based on the position of the intervertebral disc and the image characteristics of the vertebrae adjacent thereto.

Embodiments of the present invention may generate a two-dimensional sectional view of an imaged tissue based on a three-dimensional reconstruction image, and positioning, and refining of positional information of an imaged tissue based on projection of a CT value obtained in a normal direction along the centerline of the imaged tissue, and thus achieve a highly accurate and full automated extraction of clinical images, thereby providing accurate image information for doctors to quickly analyze lesions.

Preferred embodiments of the medical image processing apparatus and method of the present invention have been described above with reference to the accompanying drawings. However, the present invention is not limited to the above exemplary embodiments and drawings, and those skilled in the art can contemplate various alternatives, changes, and modification to the implementations within the scope of the technical idea, all of which fall within the protection scope of the present application.

We claim:

1. A medical image processing method, comprising:
   reconstructing a two-dimensional cross-sectional image of an imaged tissue based on a volumetric image of the imaged tissue;
   projecting a computed tomography (CT) value of the imaged tissue along a normal direction of the centerline of the imaged tissue in the two-dimensional cross-sectional image; and,
   positioning the imaged tissue based on the projection result of the CT value of the imaged tissue, wherein the imaged tissue comprises a vertebral body, the vertebral body comprising vertebras and intervertebral discs, and positioning the imaged tissue according to the projection result of the CT value of the imaged tissue comprising: obtaining a position of a peak in the result of the projection, and positioning the center position between the positions of the two adjacent peaks as an intervertebral disc position.

2. The medical image processing method according to claim 1, wherein before the projection of the CT value of the imaged tissue, the method further comprises
   binarizing the CT value of the imaged tissue in the two-dimensional cross-sectional image.

3. The medical image processing method according to claim 1, wherein the reconstructing the two-dimensional sectional image of the imaged tissue based on the volumetric image of the imaged tissue comprises:
   determining a centerline of the imaged tissue in the two-dimensional cross-sectional image based on the position of the center of the imaged tissue in the volumetric image.

4. The medical image processing method according to claim 1, wherein positioning the imaged tissue according to the projection result of the CT value of the imaged tissue further comprises:
   comparing a distance between adjacent intervertebral discs positions with a maximum threshold and a minimum threshold, and removing one of the two adjacent intervertebral disc positions when the distance between the two adjacent intervertebral disc positions is less than the minimum threshold; and add a new intervertebral disc position between the two adjacent intervertebral disc positions when the distance between the two adjacent intervertebral disc positions is greater than the maximum threshold.

5. The medical image processing method of claim 4, further comprising: dynamically determining the maximum threshold and the minimum threshold based on a median of a plurality of distances between adjacent intervertebral disc positions.

6. The medical image processing method according to claim 5, wherein the maximum threshold is determined based on a median of a plurality of distances between adjacent intervertebral disc positions of the vertebral body of the current patient.

7. The medical image processing method according to claim 5, wherein the maximum threshold is determined based on a median of a plurality of distances between adjacent intervertebral disc positions of a vertebral body of a plurality of patients retrieved from the cloud.

8. The medical image processing method according to claim 1, wherein positioning the imaged tissue according to the projection result of the CT value of the imaged tissue further comprises:

determining a position center, an inclination angle, and a thickness of the intervertebral disc based on the intervertebral disc position and the image characteristics of the vertebrae adjacent thereto.

\* \* \* \* \*